US00PP22578P2

(12) United States Plant Patent
Wilson

(10) Patent No.: US PP22,578 P2
(45) Date of Patent: Mar. 13, 2012

(54) ***DIGITALIS* PLANT NAMED 'WEDDING BELLS'**

(50) Latin Name: ***Digitalis purpurea* subsp. *heywoodii*×*Digitalis purpurea alba* peloric form'**
Varietal Denomination: Wedding Bells

(76) Inventor: Heather Kathleen Wilson, Stroud (GB)

( * ) Notice: Subject to any disclaimer, the term of this patent is extended or adjusted under 35 U.S.C. 154(b) by 0 days.

(21) Appl. No.: 12/806,025

(22) Filed: Aug. 31, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Susan McCormick Ewoldt
(74) *Attorney, Agent, or Firm* — Sonya C. Harris; Robert Beckham

(57) ABSTRACT

The new and distinct cultivar of *Digitalis* plant named 'Wedding Bells', is characterized by its peloric flower form, unique dwarf habit, prolific and repeat flowering capabilities. Its generous-sized white flowers provide a strong colour contrast with the yellow buds and together with the grey-green foliage and silver stems, create an eye catching novelty. The combination of these characteristics, together with its heat and drought resistance, establish this cultivar as one well-suited to ornamental horticultural use such as patio gardening and pot culture.

2 Drawing Sheets

Botanical designation: (*Digitalis purpurea* subsp. *heywoodii*)×(*Digitalis purpurea alba* 'peloric form').
Cultivar denomination: 'WEDDING BELLS'.

BACKGROUND OF THE INVENTION

The present Invention relates to a new and distinct cultivar of *Digitalis* plant, botanically known as *Digitalis purpurea* subsp. *heywoodii*×*Digitalis purpurea alba* 'peloric form' and hereinafter referred to by the cultivar name 'Wedding Bells'. The new *Digitalis* is the product of a planned breeding programme conducted by the Inventor in Stroud, Gloucestershire, United Kingdom in 1993 with the female, or seed parent, *Digitalis purpurea* subsp. *heywoodii* not patented, and an unnamed selection of *Digitalis purpurea alba* 'peloric form' not patented, as the male or pollen parent. The objective of the breeding programme was to create novel *Digitalis* cultivars with numerous flowers, silvery foliage and compact habit.

The new *Digitalis* was discovered as part of the selection process by the Inventor in May 2004 as a single flowering plant within the progeny of the stated cross-pollination in a controlled environment in Stroud, Gloucestershire, United Kingdom.

Asexual reproduction of the new cultivar by means of tissue culture in Hampshire, the United Kingdom, has shown that the unique features of this cultivar are stable and reproduce true to type in successive generations.

SUMMARY OF THE INVENTION

Plants of the cultivar 'Wedding Bells' have not been observed under all possible environmental conditions. The phenotype may vary somewhat with variations in environment such as temperature and light intensity without, however, any variance in genotype.

The following traits have been repeatedly observed and are determined to be the unique characteristics of 'Wedding Bells'. These characteristics in combination distinguish 'Wedding Bells' as a new and distinct *Digitalis* cultivar:

1. Dwarf and bushy plant habit.
2. Peloric in its flower form. Profuse flowering capabilities — extending late into the season on a repeat basis. Large flowers in terminal clusters of both campanulate and bilabiate form.
3. Tomentose stems and felted grey-green leaves.
4. Pronounced yellow colouration to the flower buds paling to white at maturity.

Plants of the new *Digitalis* can be compared to the female parent, the *Digitalis* subsp. *heywoodii*. Compared to plants of the subsp. *heywoodii*, plants of the cultivar 'Wedding Bells' are 30 cms shorter. The cultivar 'Wedding Bells' comprises both bilabiate and campanulate flowers on the same plant whereas the flowers of the subsp. *heywoodii* are entirely bilabiate. The terminal campanulate flowers on the cultivar 'Wedding Bells' are apically dominant whereas the bilabiate flowers on the subsp. *heywoodii* mature from the base of the raceme first.

The production of flowering laterals is greatly increased with the cultivar 'Wedding Bells' as compared to the female parent, subsp. *heywoodii*, which produces less. The colouration of the flower buds of the cultivar 'Wedding Bells' are a deeper yellow than those of the subsp. *heywoodii*, which are paler. Flowers of the cultivar 'Wedding Bells' mature to white and are rarely spotted, whereas flowers of the subsp. *heywoodii* have pink spotting within the corolla and frequently tinted pink around the corolla entrance.

Flowers of the cultivar 'Wedding Bells' are more generously proportioned than those of the subsp. *heywoodii* which are narrower and smaller overall. Fecundity on the cultivar 'Wedding Bells' is low to absent compared to the subsp. *heywoodii* which sets seed freely. The inability to set seed and repeat flowering capabilities of the cultivar 'Wedding Bells', significantly extends the flowering period over that of its female parent, the subsp. *heywoodii*.

Plants of the new *Digitalis* can be compared to the male parent, the unnamed selection of *Digitalis purpurea alba*

'pelorie form' Compared to plants of the male parent, *Digitalis* 'Wedding Bells' are perennial in habit whereas those of the male parent, *Digitalis purpurea alba* 'peloric form' are biennial.

Plants of the cultivar 'Wedding Bells' are on average 40 cms shorter than that of the male parent, *Digitalis purpurea alba.*

Compared to plants of the male parent, *Digitalis purpurea alba* 'peloric form', plants of the cultivar 'Wedding Bells' have felted grey-green foliage, tomentose stems and shortly-spaced internodes. *Digitalis purpurea alba* on the other hand, has widely-spaced internodes, coarse green foliage and green stems.

Flowers on the cultivar 'Wedding Bells' are more numerous and closely spaced than the male parent *Digitalis purpurea alba,* which has sparse widely-spaced flowers. Flowers mature, almost exclusively, to pure white on the cultivar 'Wedding Bells' — only occasionally presenting with feint khaki coloured spots within the corolla. Whereas, flowers of the male parent, *Digitalis purpurea alba,* are commonly marked with purple or khaki coloured spots — rarely presenting as pure white.

Compared to other *Digitalis* known to the Inventor, the hybrid 'Wedding Bells' is unique in its dwarf determinate form and radial arrangement of numerous flowering laterals — all of which terminate in a campanulate flower.

BRIEF DESCRIPTION OF THE PHOTOGRAPHS

The first sheet illustrates a close-up view of the new cultivar's flowers. The second sheet illustrates the overall appearance of the new cultivar. The colours are as true as it is reasonably possible to obtain in coloured reproductions of this type. Colours in the photographs may differ slightly from the colour values cited in the detailed botanical description which accurately describe the actual colours of the new *Digitalis.*

DETAILED BOTANICAL DESCRIPTION

Plants shown in the aforementioned photographs and used in the following description were grown under conditions which closely approximate commercial production conditions during the spring in an outdoor nursery in Stroud, Gloucestershire, United Kingdom. Plants were about one year old when the photographs and description were taken. In the following description, colour references are made to The Royal Horticultural Society Colour Chart, 1995 Edition, except where general terms of ordinary dictionary significance are used.

Botanical classification: *Digitalis purpurea* subsp. *heywoodii*×*Digitalis purpurea alba* 'peloric form' cultivar 'Wedding Bells'

Parentage:

*Female, or seed parent.*—*Digitalis purpurea* subsp. *heywoodii.*

*Male, or pollen parent.*—Unnamed selection of *Digitalis purpurea alba* 'peloric form'.

Propagation:

*Type.*—By tissue culture.

*Root description.*—Fine, freely branching.

Plant description:

*Form.*—Short-lived perennial, typically 3 yrs. Dwarf plant habit with dense and bushy growth. The leafy upright inflorescence develops into a narrow fan shape of branching flower stems from axillary buds. Retains a tufted rosette of foliage during winter dormancy. Plant height. Approx. 30 cms in the first year, extending to about 36 cms in subsequent years. Plant width. About 28 cms.

*Lateral stem description.*—Quantity primary laterals per plant: Average of about 8. Quantity secondary laterals per plant: Average 15-20. Length, primary laterals: Average from 15-20 cms. Length, secondary laterals: Average from 4-8 cms. Diameter, primary laterals: About 7 mm (excluding indumentum) Diameter, secondary laterals: From 2-3 mm, (excluding indumentum) Internode length: About 2-3 cms. Strength: Strong. Aspect: Slightly arching. Texture: Tomentose. Colour: Greyed-Green 194B to Greyed-Green 194C, depending on the density of indumentum.

*Foliage description.*—Arrangement: Alternate, simple along the central axis. Alternate and occasionally in opposite pairs on the primary laterals Quantity per stem: About 10 on the central axis and about 5 on the primary laterals Length: About 10 cms at maturity (excluding petiole). Width: About 5-6 cms at maturity. Shape: Ovate, tapering into the petiole. Apex: Acuminate. Base: Cuneate. Margin: Serrate. Smaller, ovate to lanceolate leaves occur in opposite pairs at the base of the secondary laterals and again singly further up. Texture when young: Upper surface, felted. Lower surface, densely felted. Texture when mature: Upper surface, puberulous, becoming tomentose into the base of the midrib and petiole. Lower surface, covered in woolly pubescence, becoming concentrated into the petiole.

*Colour.*—Developing foliage, upper surface: Green Group 138B. Developing foliage, lower surface: Greyed-Green Group 191B Fully expanded foliage, upper surface: Green Group 138A. Fully expanded foliage, lower surface: Greyed-Green Group 191B Venation pattern: Pinnate. Petiole length: 3-4 cms. Petiole width: 1-1.5 cms. Petiole texture: Upper & lower surfaces — tomentose. Petiole colour: Upper surface, Green Group 138B. Petiole colour: Lower surface, Grey-Green Group 191B.

Flower description:

*Flower arrangement and shape.*—Central axis terminates in a single apically dominant campanulate flower held at approx. 50 degrees from the vertical. Below this, an average of 3 5 bilabiate flowers are arranged alternately and in opposite pairs — opening from the base upwards and spaced between 0.5 cms and 1.5 cms apart. Frequently, a bilabiate flower occurs on a very short pedicel at the base of the apical flower. The crowded laterals which subsequently develop, telininate in clusters of between 3-4 bilabiate flowers spaced between 0.5 cms and 1.5 cms apart and having at the apex a single apically dominant campanulate flower.

*Natural flowering season.*—End April for up to 6 wks. on average in the United Kingdom. If the spent flower stems are removed, plants will respond with fresh basal growth. After approx. one month, the plants will flower on the new growth until end September approx. Flowers not persistent.

*Flower longevity on the plant.*—Individual flowers last on average 6-7 days on the plant (not including bud stage).

*Fragrance.*—None detected.

*Flower buds* (*campanulate*).—Length: About 4 cms. Diameter: About 2 cms. Shape: Ovoid. Colour: Tight buds, Yellow-Green 151 A — maturing closest to Yellow Group 5C Texture: Puberulous around the apex, becoming smooth and hairless towards the base Time to opening: 2-3 days.

*Flower buds* (*bilabiate*).—Length: About 3 cms. Diameter: About 1.5 cms. Shape: Ovoid. Form: Personate. Colour: Tight buds, Yellow-Green 151A — maturing closest to Yellow Group 5C Texture: Puberulous at the apex of the lower lip and lateral petals becoming scant and then smooth towards the base. Upper lip petal, minutely pubescent at the apex only, otherwise smooth.

*Time to opening.*—2-3 days.

*Flowers* (*campanulate*).—Length: About 4 cms. Diameter: About 3.5 cms.

*Flowers* (*bilabiate*).—Length: About 4 cms. Diameter: About 3 cms.

*Petals, campanulate flowers.*—Arrangement: Fused at the corolla base separating into lobes at the apex. Each aspect of equal length having typically 5-6 fused petals per flower with a maximum of 8 recorded. Length: About 4 cms. Width: About 1.5 cms. Shape: Oval, undulating from the base giving a ribbed appearance Apex: rounded becoming undulate at maturity. Margin: Entire. Texture outer surface: Puberulous at the apex becoming smooth and hairless towards the base. Texture inner surface: Conspicuous hairs, 3 mm long line the apex, becoming smooth and hairless towards the base. Colour exterior surface: When opening, Yellow Group 8C — suffused Yellow Group 8B. Fully open: Yellow Group 8D — paling to White Group 155A at maturity Colour interior surface: When opening, Yellow Group 8B Fully open: Yellow Group 8D — paling to White Group 155A at maturity. Very occasionally, a sprinkling of feint khaki spots line the corolla.

*Petals bilabiate flowers.*—Arrangement: Having four upper petals fused towards the base and One lower lip petal. Length, upper lip petals: About 3 cms Length lateral petals: About 3.5 cms Length, lower lip petal: About 4 cms Width, upper petals: About 2 cms Width, lower lip petal: About 1.8 cms. Shape: Oval but with noticeable, centrally-placed ridge to the upper petals, flattening into the lobe. Apex: Rounded, becoming undulate at maturity on the lower lip petal. Margin: Entire. Texture: Exterior, upper lip petal, minutely pubescent at the apex only, otherwise smooth. Exterior, lateral petals: Puberulous at the apex, becoming scant and then smooth towards the base. Texture: Interior, upper petals, smooth with minute marginal hairs. Texture: Exterior, lower lip petal. Puberulous at the apex, becoming smooth and hairless towards the base. Texture: Interior, lower lip petal. Conspicuous hairs, 3 mm long line the apex, becoming smooth and hairless towards the base.

*Colour upper petals.*—When opening, outer surface: Yellow Group 8C. Fully open: Yellow Group 8D paling to White Group 155A at maturity When opening, inner surface: Yellow Group 8C. Fully open: Yellow Group 8D paling to White Group 155A at maturity.

*Colour lateral petals.*—When opening, outer surface: Yellow Group 8C with minor Yellow Group 8B shadings. Fully open: Yellow Group 8D paling to White Group 155A at maturity. When opening, inner surface: Yellow Group 8B. Fully open: Yellow Group 8D paling to White Group 155A at maturity.

*Colour lower lip petal.*—When opening, outer surface: Yellow Group 8C with minor Yellow Group 8B shadings. Fully open: Yellow Group 8D paling to White Group 155A at maturity When opening, inner surface: Yellow Group 8B. Fully open: Yellow Group 8D paling to White Group I 55A at maturity Very occasionally, a sprinkling of feint khaki coloured spots appear.

*Sepals.*—Arrangement/quantity per flower: Between 5 & 8 on the terminal flowers, not fused. 5 on the bilabiate flowers, not fused Length: About 1.5 cms. Width: About 1 cm. Shape: Ovate. Apex: Acute. Base: Acute. Margin: Entire. Texture, upper surface smooth with minute marginal hairs. Texture, puberulent becoming tomentose towards the base. Colour, upper surface: Yellow-Green Group 146B. Yellow-Green 146C basal shading Colour, lower surface: Yellow-Green Group 146B.

*Peduncles.*—Length: About 20 cms. Diameter: About 7 mm (excluding indumentum) Aspect: Slightly arching. Strength: Strong. Texture: Tomentose. Colour: Greyed-Green 194C.

*Pedicels.*—Length: About 0.5-1.5 cms. Diameter: About 1 mm (excluding indumentum) Aspect: Slightly arching. Strength: Strong. Texture: Tomentose. Colour: Greyed-Green 194C.

Reproductive organs:

*Stamens.*—Quantity per terminal flower: 5-8. Arrangement: Inserted individually at the base of the corolla around the pistil Filament length: About 13 mm. Filament colour: White Group 155D (translucent quality).

*Stamens.*—Quantity per stem flower: 4. Arrangement: Didynamous. Filament length: About 11 mm for the shorter pair to 13 mm for the longer pair Filament colour: White Group 155D (translucent quality).

*Anthers.*—Shape: Reniform. Anther length: About 3 mm. Anther colour: Yellow Group 9D. Pollen amount: Sparse to moderate. Pollen colour: Yellow-White Group 158D.

*Pistils.*—Quantity per flower: One. Pistil length: About 2.5 cms (in both apical and stem flowers). Stigma form: Bibbed, occasionally tripartite. Stigma colour: White Group 155D (opaque quality). Style length: About 1.3 cms. Style colour: White Group 155D (translucent quality). Ovary colour: Yellow-Green Group 146C, with Yellow-Green 146D basal shading Ovary Form: Septate.

*Fruit/seeds.*—Fecundity very low. The majority of seed capsules having a 'puckered' appearance containing little or no seed as a result of self-fertilization (self incompatible). Any seed produced having low fertility and short viability. Fertility is however restored by pollen from *Digitalis purpurea* varieties — with which it is compatible. The resultant hybrids, in the main, being 'not of type' with only the occasional individual resembling the seed parent.

*Seed colour.*—Brown Group 200C.

Disease/pest resistance: Plants of the new *Digitalis* have been noted to be resistant to aphids Drought resistance: Plants of the new *Digitalis* have been noted to tolerate moderate drought High temperature tolerance: Plants of the new *Digitalis* have been observed to tolerate temperatures up to 30 degrees C.

Hardiness: Plants of the new *Digitalis* have been observed to be hardy to about −6 degrees C.

It is claimed:

1. A new and distinct cultivar of *Digitalis* plant named "Wedding Bells", as illustrated and described characterised by a dwarf and bushy plant habit, peloric in its flower form, profuse flowering capabilities — extending late into the season on a repeat basis, large flowers in terminal dusters of both campanulate and bilabiate form, tomentose stems and felted grey-green leave and pronounced yellow colouration to the flower buds paling to white at maturity.

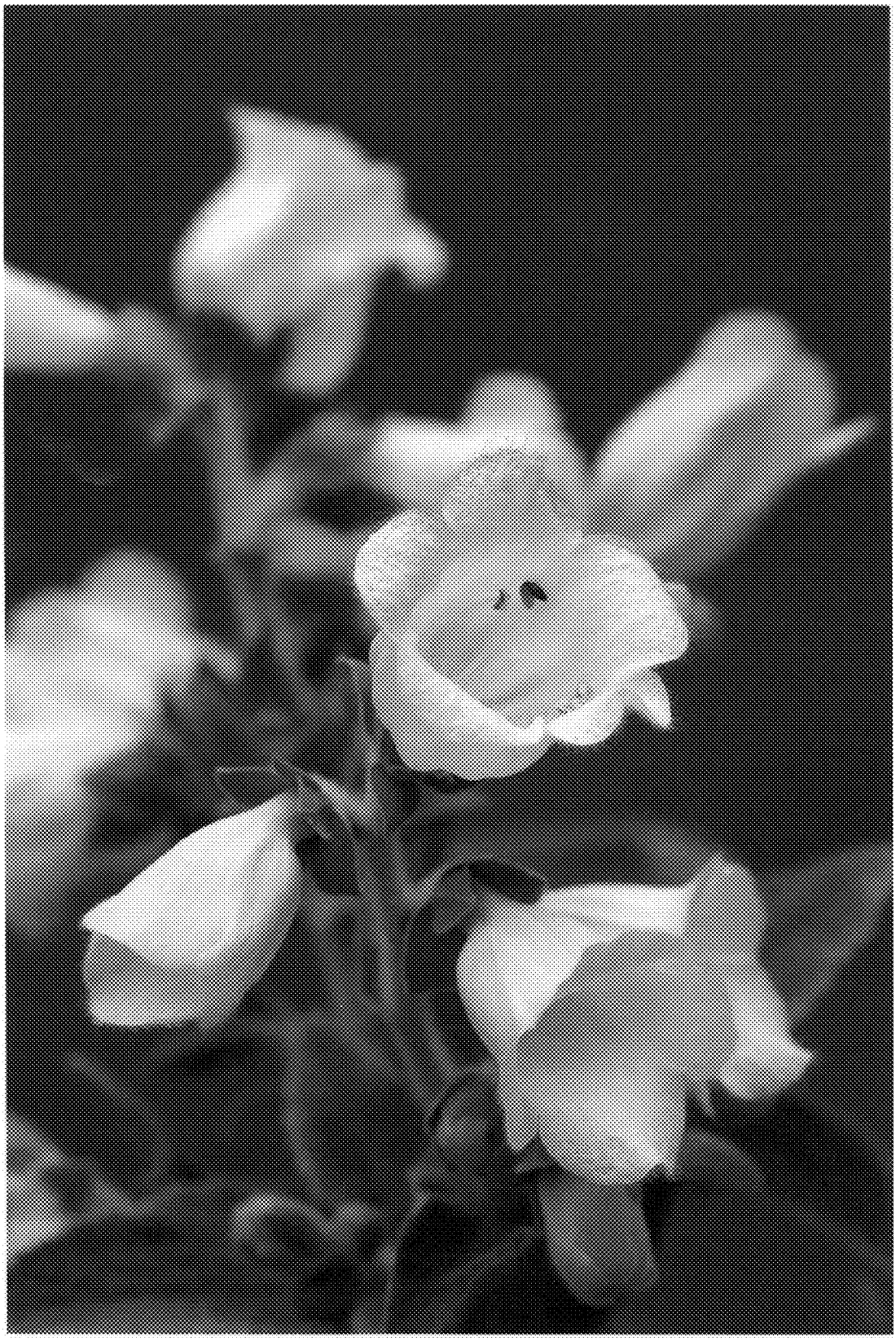

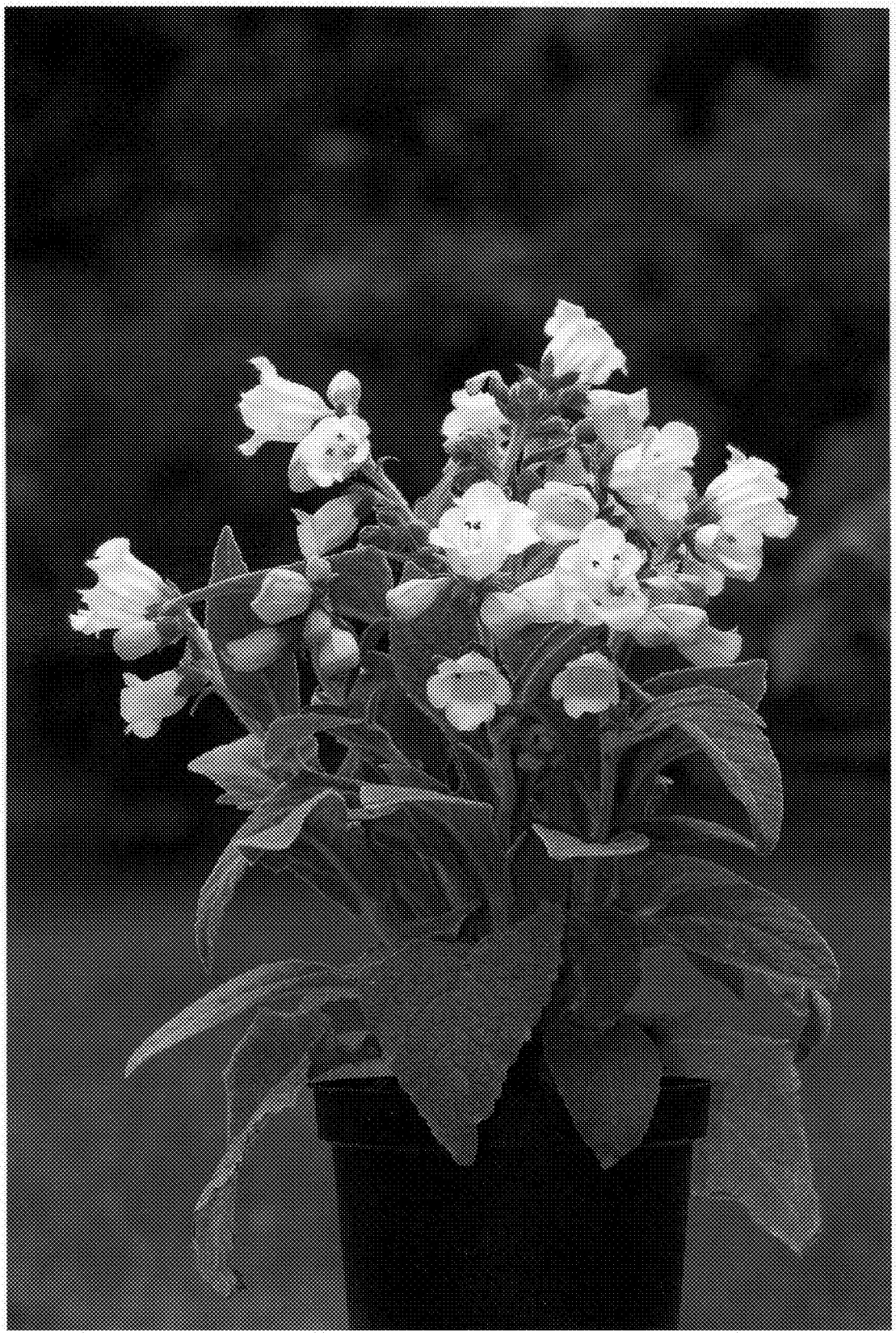

* * * * *